United States Patent
Klein et al.

(10) Patent No.: US 7,920,061 B2
(45) Date of Patent: Apr. 5, 2011

(54) CONTROLLING AN ALARM STATE BASED ON THE PRESENCE OR ABSENCE OF A CAREGIVER IN A PATIENT'S ROOM

(75) Inventors: Keith Klein, Washington, DC (US); Steven Falk, Baltimore, MD (US)

(73) Assignee: General Electric Company, Schenectady, NY (US)

( * ) Notice: Subject to any disclaimer, the term of this patent is extended or adjusted under 35 U.S.C. 154(b) by 233 days.

(21) Appl. No.: 12/324,050

(22) Filed: Nov. 26, 2008

(65) Prior Publication Data
US 2010/0127866 A1    May 27, 2010

(51) Int. Cl.
*G08B 13/00* (2006.01)

(52) U.S. Cl. ............... 340/541; 340/573.1; 340/825.36; 340/506; 340/825.49

(58) Field of Classification Search ............ 340/541, 340/573.1, 825.49, 506, 310.11, 524, 525, 340/825.36, 507, 693.2, 311.2, 326, 328, 340/331, 332, 333
See application file for complete search history.

(56) References Cited

U.S. PATENT DOCUMENTS

| | | | | |
|---|---|---|---|---|
| 4,366,821 A | * | 1/1983 | Wittmaier et al. ............ 600/532 |
| 4,947,152 A | * | 8/1990 | Hodges ...................... 340/573.4 |
| 7,327,219 B2 | * | 2/2008 | Lederer, IV ............. 340/286.07 |
| 2002/0044043 A1 | * | 4/2002 | Chaco et al. ............. 340/286.07 |
| 2002/0067257 A1 | * | 6/2002 | Thomas et al. ............... 340/540 |
| 2003/0019165 A1 | * | 1/2003 | Gallant et al. ................. 52/36.4 |
| 2004/0189475 A1 | * | 9/2004 | Cooper et al. ............. 340/573.1 |
| 2005/0168341 A1 | * | 8/2005 | Reeder et al. ............. 340/573.1 |
| 2007/0040692 A1 | * | 2/2007 | Smith et al. ............... 340/573.1 |
| 2007/0057805 A1 | * | 3/2007 | Gomez ..................... 340/691.2 |
| 2007/0080801 A1 | * | 4/2007 | Weismiller et al. ...... 340/539.13 |
| 2008/0180228 A1 | * | 7/2008 | Wakefield et al. ....... 340/310.11 |
| 2008/0204258 A1 | * | 8/2008 | Dayton et al. ............... 340/600 |

* cited by examiner

*Primary Examiner* — George A Bugg
*Assistant Examiner* — Hoi C Lau
(74) *Attorney, Agent, or Firm* — Andrus, Sceales, Starke & Sawall, LLP

(57) ABSTRACT

Systems and methods for controlling an alarm state, such as volume, based on the presence or absence of a caregiver in a patient's room. More specifically, a local sound producing device provides an audible alarm within a room when a caregiver is in the room, while a remote sound producing device provides an audible alarm external of the room when the caregiver is not in the room. Accordingly, volume levels of the sound producing devices depend on the sensed presence or absence of the caregiver within the room. For example, when the caregiver leaves the room, the local sound producing device is deactivated and/or the remote sound producing device is activated, thereby allowing the patient to enjoy a more relaxed environment within the room, yet still continue to be monitored. Conversely, when the caregiver enters the room, the local sound producing device is activated and/or the remote sound producing device is deactivated, thereby allowing the caregiver to monitor the patient when within the room, yet allow decreased monitoring external of the room.

23 Claims, 2 Drawing Sheets

CONTROLLING AN ALARM STATE BASED ON THE PRESENCE OR ABSENCE OF A CAREGIVER IN A PATIENT'S ROOM

BACKGROUND

In general, the inventive arrangements relate to systems and methods for controlling an alarm state, such as volume, emitted by audible sound producing devices located within and external of a room of a medical patient. More specifically, they relate to systems and methods that control the volume of alarms based on the presence or absence of caregivers within the patient's room.

In healthcare facilities, it is, of course, very common to have local alarm producing devices located in the room of a patient. For example, an alarm producing device may be incorporated into a patient monitor to monitor certain conditions of the patient. Oftentimes, the patient monitor includes an audible alarm that sounds when the condition being monitored is outside of certain predetermined limits. That alarm is generally sufficiently loud and conveys a sense of urgency, such that there is an immediate recognition of an alarm condition that enables caregivers to take appropriate action to understand and alleviate the alarm condition.

Alternatively and/or additionally, other alarm producing devices may also be included within a patient's room, such as, for example, a bed alarm, other medical equipment, a ventilator, infusion pump, and/or the like, and alarms may be emitted based on sensed parameters, in response, for example, to a condition of a medical apparatus used in connection with the patient, some incident related to the medical apparatus, such as a power failure or other failure, an undesired or noteworthy change in the patient's environment, and/or the like.

One of the problems, however, with such audible alarms is that the alarm producing device, such as within the patient monitor, is, for convenience, often located within the room where the patient is located, and they are often located in relative close proximity to the patient. As such, the sound of the alarm can create an immediate stimulus to the patient and have a negative impact thereon—i.e., numerous alarm sounds can have a negative physiological impact on the patient and create additional stress in the patient, who may already be in a stressed condition.

As a result, when a caregiver is present in the patient's room, many alarm producing devices have a mute function so that the caregiver can immediately mute the sound of the alarm. However, if the caregiver is not present at the time of the audible alarm, then the continued sound of the alarm can create the aforementioned negative effect on the patient.

Accordingly, it would be particularly advantageous to have a device and/or method that can alleviate the negative stimulus that can be created by an audible alarm within a patient's room whenever a caregiver is not present within the room, yet still retain the safety of allowing the caregivers to hear and/or recognize the audible alarm from the sound producing devices within the patient's room.

SUMMARY OF THE INVENTIVE ARRANGEMENTS

Accordingly, with the present invention, system and method embodiments are provided to control the volume of audible alarm sounds emitted from sound producing devices depending on the presence or absence of a caregiver within a patient's room.

For convenience, some of the embodiments will be described with respect to a sound producing device incorporated into a patient monitor that continually monitors a condition of a patient. However, it can also be noted that the inventive arrangements are equally applicable to other sound producing devices located within the patient's room, and which also provide an audible alarm, including, for example, but not limited to, sound producing devices incorporated into other medical apparatuses, such as an anesthesia machine, infusion pump, and/or any other device located within the patient's room wherein the sound producing device emits sound indicating an alarm condition and/or indicates the condition or status of a piece of medical equipment being used in the patient's room, such as a power failure, probe dislodgement, and/or other undesirable conditions.

In any event, the normal volume of sound emitted from a sound producing device incorporated into, for example, a patient monitor, is often intentionally loud and intended to gain the immediate attention of a caregiver.

Oftentimes, there is also a remote sound producing device located outside the patient's room and preferably in a common room, such as a nurse's station for example, where the audible alarm sounds emitted by the remote sound producing device can be continually monitored by the caregivers located outside of the patient's room.

A sensing device is provided to sense the presence or absence of a caregiver within the patient's room. The sensing device communicates that information to a volume control system, such as in the patient monitor, such that the volume level of the sound emitted to indicate an alarm condition is changed depending on the presence or absence of the caregiver in the patient's room. Thus, when a caregiver leaves the patient's room, the sensing device alerts the volume control system and the normal and/or loud sound of the alarm thereafter emitted by the local sound producing device within the patient's room is reduced, possibly to a zero level condition, whereby no sound is emitted by the patient monitor and into the patient's room during an otherwise alarm condition.

The sensing device can be any of a variety of devices, including, for example, a motion sensor that determines the presence or absence of a caregiver in the patient's room by sensing a motion, or lack of motion, thereof. The sensing device can also be a manual device located within the patient's room, such as on a patient monitor or other medical apparatus or support apparatus, that can be advantageously turned to a remote mode whenever the caregiver leaves the patient's room.

The remote sound producing device, however, located external of the patient's room, can continue to emit a sound indicative of the alarm condition, particularly so that the audible alarm can be noted by caregivers outside the patient's room and who still need to take appropriate corrective action.

Conversely, as the caregiver returns to the patient's room, the sensing device determines the caregiver is again present in the room and signals the volume control system to return the volume level of the alarm of the local sound producing device to its original, loud volume.

Thus, by the present invention, normal, traumatic, loud alarm volumes can be reduced, or eliminated altogether, whenever a caregiver is not present in a patient's room, so that the physiological impact of the loud alarm on the patient can be eliminated, yet for which there continues to be monitoring of the applicable alarm conditions by audible alarms located outside of the patient's room.

These, and other, features and advantages of the present invention will become more readily apparent from the following detailed description, particularly when also read in conjunction with the drawings contained herein.

DETAILED DESCRIPTION OF THE INVENTIVE ARRANGEMENTS

Figure 1:
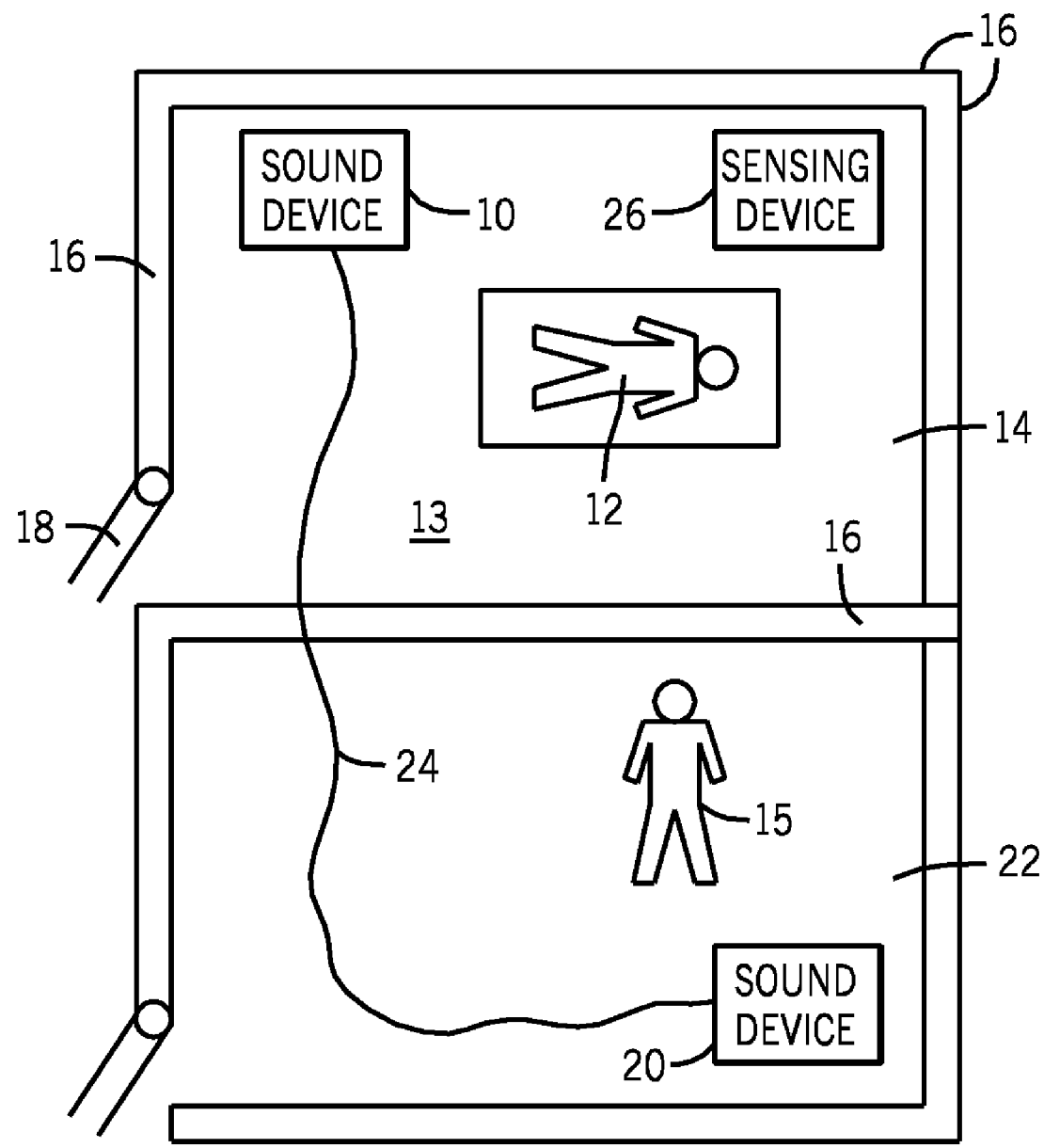
FIG. 1 is a schematic view of a system of the inventive arrangements, illustrating typical locations of components.

Referring now to FIG. 1, a schematic view of the system of the present invention includes a local sound producing device 10, such as incorporated into a patient monitor, that monitors certain functions of the patient 12 or the patient's environment 13 or the patient's room 14. As is conventional, for example, a patient monitor has a number of alarm functions that provide an audible alarm when a particular sensed condition is outside of certain prescribed limits, so that a caregiver 15 can be alerted to the existence of an alarm condition and take corrective action, as necessary and/or desired. As indicated, the local sound producing device 10 can be incorporated into other types of apparatuses within the patient's room 14, including, for example, a medical apparatus such as an anesthesia machine, infusion pump, and/or any other device that provides an audible alarm upon the occurrence of a condition effecting the patient 12, the patient's environment 13, the patient's room 14, and/or the status of some other equipment used in connection with monitoring and/or caring for the patient 12 and/or the like.

As can be seen, the local sound producing device 10 is located in the patient's room 14, along with the patient 12, and it is normally located in relative close proximity to the patient 12. The patient's room 14 typically has walls 16 to enclose same and give the patient 12 privacy, as well as a door 18 for ingress and egress of various caregivers 15 and/or the like that attend to the patient 12 while the patient 12 is in the patient's room 14.

There is also a remote sound producing device 20 that is located external to the patient's room 14—i.e., in a separate room 22. The remote sound producing device 20 often provides an alarm simultaneous with the audible alarms provided by the local sound producing device 10 within the patient's room 14. In essence, therefore, the audible alarm sounds emitted by the local sound producing device 10 are transmitted to the remote location external of the patient's room 14, and the signals generating the audible alarm can be transmitted by hard wires 24 and/or by some wireless system (not shown) thereto. Typically, the separate room 22 may be a central nurse's station, for example, or another locale where caregivers 15 are stationed to attend to other duties while maintaining watch over the audible alarms that may be emitted by and/or from the remote sound producing device 20.

Within the patient's room 14, there is also a sensing device 26 that can sense the presence or absence of the caregiver 15. Accordingly, in an exemplary embodiment, the sensing device 26 is a motion sensor that is located within the patient's room 14 such that movement of the caregiver 15 into, within, and/or out of the patient's room 14 is detected. More specifically, the sensing device 26 can detect movement of the caregiver 15 into the patient's room 14 in order to determine that the caregiver 15 is present therewithin, while a lack of movement detected by the sensing device 26 determines that the caregiver 15 is absent from the patient's room 14. Thus, in accordance with the sensing device 26, a determination is made as to whether the caregiver 15 is present or absent from the patient's room 14. In the figure, for example, the caregiver 15 is shown absent from the patient's room 14 and in the separate room 22.

In an alternate embodiment, the sensing device 26 is a manually operated device, such as a push-button, that the caregiver 15 can activate or deactivate upon ingress into or egress out of the patient's room 14, such that the sensing device 26 can still determine whether or not the caregiver 15 is within the patient's room 14. In an exemplary embodiment, for example, the manually operated device can be a push-button incorporated into a patient monitor (not shown in FIG. 1) incorporating the local sound producing device 10. In such a manner, the caregiver 15 can change the mode of operation of the local sound producing device 10 and/or remote sound producing device 20 when entering and/or exiting the patient's room 14. When the caregiver 15 is inside the patient's room 14, for example, as detected by the sensing device 26, then the local sound producing device 10 is active and/or the remote sound producing device 20 is inactive, whereas when the caregiver 15 is not inside the patient's room 14, as detected by the sensing device 26, then the local sound producing device 10 is inactive and/or the remote sound producing device 20 is active.

Figure 2:
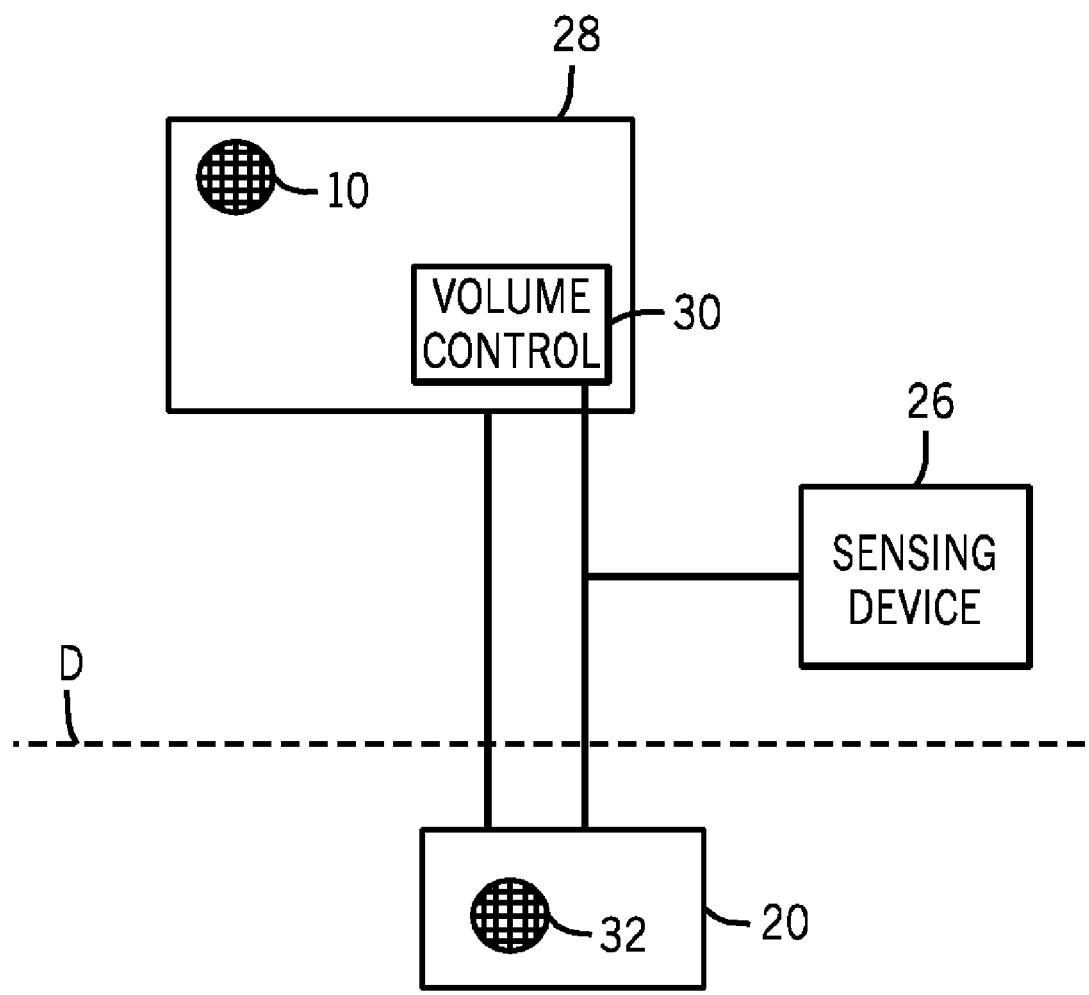
FIG. 2 is a schematic view of the function the inventive arrangements.

Referring now to FIG. 2, taken along with FIG. 1, a schematic view illustrates various components of the inventive arrangements. As can be seen, the local sound producing device 10 is present and separated from the remote sound producing device 20, particularly by a wall, indicated by a dotted line D. Preferably, the local sound producing device 10 is incorporated into an instrument 28, such as a patient monitor, such that the local sound producing device 10 provides an audible alarm when some condition of the patient 12 (see FIG. 1) has been sensed to be outside of certain limits. There is also a volume control system 30 preferably incorporated into the instrument 28 to control the volume of the local sound producing device 10 and/or instrument 28. The volume control system 30 can be carried out in hardware and/or software and/or the like, and it can be incorporated into either the local sound producing device 10 (as depicted) and/or into the remote sound producing device 20 (not shown), and/or some other design combination thereof.

Accordingly, the function of the present invention can now be explained. More specifically, the sensing device 26 senses and determines the presence or absence of the caregiver 15 inside the patient's room 14. As such, whenever the caregiver 15 is present in the patient's room 14, the local sound producing device 10 within the patient's room 14 carries out its normal function of emitting certain loud audible sounds indicative of a particular alarm condition. The remote sound producing device 20, on the other hand, may or may not be activated to simultaneously emit sounds via its speaker 32 along with the local sound producing device 10 of the instrument 28. As such, the sounds emitted by the local sound producing device 10 within the patient's room 14 can be immediately heard by the caregiver 15 within the patient's room 14, and who can then take remedial steps as necessary and/or desired to alleviate the alarm situation, including muting the alarm sounds at the local sound producing device 10.

If/when, however, the caregiver 15 leaves the patient's room 14, then the sensing device 26 determines that the caregiver 15 is now absent from the patient's room 14 and signals that condition to the volume control system 30 in the instrument 28. The volume control system 30 thus reduces the audible level of the sounds emitted by the local sound producing device 10 into the patient's room 14. That level may be reduced to a lower level, or to a zero level where no sound or minimal sound is emitted from the local sound producing device 10 upon detection of an alarm condition.

The sensing device 26, at the same time, communicates with the remote sound producing device 20 to insure that the remote sound producing device 20 is activated so that any alarm condition sensed about the patient 12, the patient's environment 13, the patient's room 14, and/or the like, produces an audible sound that is emitted by the remote sound producing device 20, so that the caregiver 15, if located at a location external of the patient's room 14, can now still hear the alarm and take appropriate action. If the remote sound producing device 20 has remained continually activated while the caregiver 15 was in the patient's room 14, then the sensing device 26 need not activate the remote sound producing device 20, but it could, if desired, still verify that the remote sound producing device 20 is still activated.

By these embodiments, the local sound producing device 10 within the patient's room 14 is preferably prevented from emitting alarm sounds at a normal, loud level when the caregiver 15 is not present therewithin the patient's room 14, as opposed to simply muting all alarm sounds after such sounds have already been emitted at that loud level. Accordingly, some of the embodiments functionally act in advance of, or otherwise prior to, the emitting of the loud volume sounds, rather than by muting or reducing the sound level after the sound has already been emitted.

As can now be seen, the reverse function is also carried out by the inventive arrangements—i.e., if/when the caregiver 15 re-enters the patient's room 14, the sensing device 26 senses the presence of the caregiver 15 and signals the volume control system 30 to return the sound volume level back to the normal, loud sound conventionally emitted by the local sound producing device 10. Since the caregiver 15 is already present within the patient's room 14, the volume control system 30 can be configured to mute or silence or reduce the volume of audible sounds at the remote sound producing device 20, as the caregiver 15 can likely already attend to the needs of the patient 12.

In accordance with the foregoing, a technical effect of the inventive arrangements is to control an alarm state, such as volume, based on the presence or absence of the caregiver 15 within the patient's room 14. More specifically, the local sound producing device 10 provides an audible alarm within the patient's room 14 when the caregiver 15 is therewithin, while a remote sound producing device 20 provides an audible alarm external of the patient's room 14 when the caregiver is not therewithin. Accordingly, volume levels of the sound producing devices 10, 20 depend on the sensed presence or absence of the caregiver 15 within the patient's room 14.

Those skilled in the art will readily recognize that numerous adaptations and modifications can be made to the inventive arrangements, yet all of which still fall within the scope and spirit of the invention, particularly as defined in the following claims. Accordingly, the invention is to be limited only by the following claims and their equivalents.

What is claimed is:

1. A system for controlling volume, comprising:
   a local sound producing device configured to provide an audible alarm within a room;
   a remote sound producing device configured to provide an audible alarm external of the room;
   a sensing device configured to detect a presence or absence of a caregiver in the room; and
   a volume control system configured to change a volume of the local sound producing device and/or remote sound producing device based on the presence or absence of the caregiver in the room,
   wherein the volume control system is configured to decrease the volume of the local sound producing device when the sensing device detects the absence of the caregiver in the room and increase the volume of the local sound producing device when the sensing device detects the presence of the caregiver in the room.

2. A system for controlling volume, comprising:
   a local sound producing device configured to provide an audible alarm within a room;
   a remote sound producing device configured to provide an audible alarm external of the room;
   a sensing device configured to detect a presence or absence of a caregiver in the room; and
   a volume control system configured to change a volume of the local sound producing device and/or remote sound producing device based on the presence or absence of the caregiver in the room,
   wherein the volume control system is configured to increase the volume of the remote sound producing device when the sensing device detects the absence of the caregiver in the room, and decrease the volume of the remote sound producing device when the sensing device detects the presence of the caregiver in the room.

3. The system of claim 1, wherein the volume control system decreases the volume of the local sound producing device to a zero level.

4. The system of claim 2, wherein the volume control system decreases the volume of the remote sound producing device to a zero level.

5. The system of claim 1, wherein the local sound producing device is deactivated when the sensing device detects the absence of the caregiver in the room.

6. The system of claim 2, wherein the remote sound producing device is deactivated when the sensing device detects the presence of the caregiver in the room.

7. The system of claim 1, wherein the local sound producing device is activated when the sensing device detects the presence of the caregiver in the room.

8. The system of claim 2, wherein the remote sound producing device is activated when the sensing device detects the absence of the caregiver in the room.

9. The system of claim 1, wherein the local sound producing device contains the volume control system.

10. The system of claim 2, wherein the remote sound producing device contains the volume control system.

11. The system of claim 1, wherein the local sound producing device is configured to be incorporated into a patient monitor in the room.

12. The system of claim 1, wherein the sensing device is a manual device configured to be activated by the caregiver.

13. The system of claim 1, wherein the local sound producing device is configured to be incorporated into a patient monitor in the room and the sensing device is a manual device configured to be activated by the caregiver.

14. The system of claim 13, wherein the patient monitor contains the manual device.

15. The system of claim 1, wherein the sensing device comprises a motion sensing device that is configured to detect the presence or absence of the caregiver in the room.

16. A method for controlling volume, comprising:
   providing a local sound producing device configured to provide an audible alarm within a room;

providing a remote sound producing device configured to provide an audible alarm external of the room;
detecting a presence or absence of a caregiver in the room;
changing a volume of the local sound producing device and/or remote sound producing device based on the presence or absence of the caregiver in the room;
decreasing the volume of the local sound producing device when the caregiver is not in the room; and
increasing the volume of the local sound producing device when the caregiver is in the room.

17. A method for controlling volume, comprising:
providing a local sound producing device configured to provide an audible alarm within a room;
providing a remote sound producing device configured to provide an audible alarm external of the room;
detecting a presence or absence of a caregiver in the room;
changing a volume of the local sound producing device and/or remote sound producing device based on the presence or absence of the caregiver in the room
increasing the volume of the remote sound producing device when the caregiver is not in the room; and
decreasing the volume of the remote sound producing device when the caregiver is in the room.

18. The method of claim 16, further comprising:
decreasing the volume of the local sound producing device to a zero level.

19. The method of claim 17, further comprising:
decreasing the volume of the remote sound producing device to a zero level.

20. The method of claim 16, further comprising:
deactivating the local sound producing device when the caregiver is not in the room.

21. The method of claim 17, further comprising:
deactivating the remote sound producing device when caregiver is in the room.

22. The method of claim 16, further comprising:
activating the local sound producing device when the caregiver is in the room.

23. The method of claim 17, further comprising:
activating the remote sound producing device when the caregiver is not in the room.

* * * * *